(12) United States Patent
Osborne et al.

(10) Patent No.: US 7,402,171 B2
(45) Date of Patent: Jul. 22, 2008

(54) PROSTHETIC VALVE THAT PERMITS RETROGRADE FLOW

(75) Inventors: Thomas A. Osborne, Bloomington, IN (US); Brian C. Case, Bloomington, IN (US); Mark W. Bleyer, West Lafayette, IN (US); Ram H. Paul, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 587 days.

(21) Appl. No.: 10/797,449

(22) Filed: Mar. 10, 2004

(65) Prior Publication Data

US 2004/0225352 A1 Nov. 11, 2004

Related U.S. Application Data (60) Provisional application No. 60/454,249, filed on Mar. 12, 2003, provisional application No. 60/488,138, filed on Jul. 16, 2003.

(51) Int. Cl.
*A61F 2/24* (2006.01)
(52) U.S. Cl. .................................... 623/1.24
(58) Field of Classification Search ............... 623/1.24, 623/1.26, 2.1, 2.11–2.19
See application file for complete search history.

(56) References Cited

U.S. PATENT DOCUMENTS

| | | | | |
|---|---|---|---|---|
| 3,737,919 A * | 6/1973 | Child | ......................... | 623/2.23 |
| 4,328,592 A | 5/1982 | Klawitter | | |
| 4,580,568 A | 4/1986 | Gianturco | | |
| 4,731,075 A * | 3/1988 | Gallo Mezo et al. | ........ | 623/2.17 |
| 4,787,901 A * | 11/1988 | Baykut | ....................... | 623/1.26 |
| 5,197,980 A * | 3/1993 | Gorshkov et al. | ............. | 623/2.1 |
| 5,413,599 A * | 5/1995 | Imachi et al. | ............... | 623/1.24 |
| 5,628,791 A | 5/1997 | Bokros et al. | | |
| 5,641,324 A | 6/1997 | Bokros et al. | | |
| 5,908,452 A | 6/1999 | Bokros et al. | | |
| 6,027,525 A | 2/2000 | Suh et al. | | |
| 6,059,826 A * | 5/2000 | Bokros et al. | ............... | 623/2.11 |
| 6,200,336 B1 | 3/2001 | Pavcnik et al. | | |
| 6,231,598 B1 | 5/2001 | Berry et al. | | |
| 6,287,334 B1 | 9/2001 | Moll et al. | | |
| 6,299,635 B1 | 10/2001 | Frantzen | | |
| 6,464,720 B2 | 10/2002 | Boatman et al. | | |
| 6,482,228 B1 | 11/2002 | Norred | | |
| 6,494,909 B2 | 12/2002 | Greenhalgh | | |
| 6,508,833 B2 | 1/2003 | Pavcnik et al. | | |
| 6,676,698 B2 | 1/2004 | McGuckin, Jr. et al. | | |
| 6,790,237 B2 * | 9/2004 | Stinson | .................... | 623/23.68 |
| 6,958,076 B2 * | 10/2005 | Acosta et al. | ............... | 623/1.24 |
| 7,125,418 B2 * | 10/2006 | Duran et al. | ................ | 623/1.24 |
| 2001/0039450 A1 | 11/2001 | Pavcnik et al. | | |
| 2002/0055772 A1 | 5/2002 | McGuckin, Jr. et al. | | |

(Continued)

OTHER PUBLICATIONS http://dictionary.reference.com/browse/through.*
Merriam-Webster's Collegiate Dictionary Tenth Edition, 2001, p. 1226.*

*Primary Examiner*—Corrine McDermott
*Assistant Examiner*—Cheryl Miller
(74) *Attorney, Agent, or Firm*—Buchanan Intellectual Property Office LLC (57) ABSTRACT

A prosthetic valve for regulating fluid flow through a body vessel is provided. The valve includes an expandable support frame and a valve leaflet, and includes at least one opening that permits a controlled amount of retrograde flow through the valve when the valve is in a closed configuration.

11 Claims, 7 Drawing Sheets

U.S. PATENT DOCUMENTS

2002/0123802 A1* 9/2002 Snyders ............... 623/2.18
2002/0177894 A1 11/2002 Acosta et al.
2003/0055492 A1* 3/2003 Shaolian et al. ............ 623/1.24
2003/0181974 A1 9/2003 Xie et al.

* cited by examiner

FIG. 23 ial Appli-
cation Ser. No. 60/454,249, filed on Mar. 12, 2003, and U.S.

PROSTHETIC VALVE THAT PERMITS RETROGRADE FLOW

CROSS-REFERENCE TO RELATED APPLICATIONS

This application claims priority to U.S. Provisional Application Ser. No. 60/454,249, filed on Mar. 12, 2003, and U.S. Provisional Application Ser. No. 60/488,138, filed on Jul. 16, 2003, each of which is hereby incorporated into this disclosure in its entirety.

FIELD OF THE INVENTION

The present invention relates to medical devices. More particularly, the invention relates to intraluminal valve prostheses.

BACKGROUND OF THE INVENTION

Many vessels in animal bodies transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction and close to prevent fluid flow in a reverse direction, i.e., retrograde flow. The valves can change from an open position in response to a variety of circumstances, including changes in the cross-sectional shape of the vessel and the fluid pressure within the vessel.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, and can lead to discomfort and possibly ulcers in the legs and ankles.

Current treatments for venous valve insufficiency include the use of compression stockings that are placed around the leg of a patient in a effort to force the vessel walls radially inward to restore valve function. Surgical techniques are also employed in which valves can be bypassed, eliminated, or replaced with autologous sections of veins having competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, the use of stents has been extended to treat aneurysms and to provide occlusion devices, among other uses.

Recently, prosthetic valves that are implantable by minimally invasive techniques have been developed. Frequently, a graft member is attached to a support frame and provides a valve function to the device. For example, the graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, U.S. patent application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety. In other examples of prosthetic valves, a tube that terminates in leaflets is attached to one or more support frames to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Natural valves can be somewhat 'leaky', allowing a relatively small quantity of fluid to flow in a reverse direction when the valve is in a closed position. It is believed that this leakiness is beneficial for several reasons. For example, it is believed that a small amount of retrograde flow limits the pooling of blood around the natural valve during periods of low pressure, which can reduce the formation of thrombus adjacent the valve leaflets and, therefore, increase the effective lifetime of the valve.

Prior art prosthetic valves, however, do not permit a controlled amount of retrograde flow. Indeed, most prior art valves have been designed to prevent leakage as much as possible. Accordingly, there is a need for a prosthetic valve that permits a controlled amount of retrograde flow.

SUMMARY OF THE INVENTION

A medical device according to the invention provides a valve for regulating fluid flow through a body vessel. The device is particularly well-suited for percutaneous delivery through a body vessel to a point of treatment, and comprises a prosthetic venous valve in an illustrative embodiment. The valve permits a controlled quantity of retrograde flow to flow through the device when the valve is in its closed configuration.

The medical device includes a support frame, such as an endoluminal stent, that has radially compressed and radially expanded configurations. The support frame can comprise any suitable support frame, including self-expandable, balloon expandable, wire, tube, metal, polymeric, composite and other types of support frames known in the art.

The device includes at least one leaflet attached to the support structure. The leaflet provides a valve function to the device. In one embodiment, the leaflet provides the valve function by moving between first and second positions while remaining attached to the support frame. In one position, the leaflet substantially blocks the lumen of the vessel, while the lumen is substantially open when the leaflet is in the second position. Thus, the leaflet permits fluid flow through the vessel in a first direction when in the first position, and substantially prevents fluid flow through the vessel in a second, opposite direction when in the second position. The leaflet can be formed of a bioremodellable material, such as small intestine submucosa (SIS) or other extracellular matrix (ECM) material.

The device includes an opening that permits a controlled amount of fluid flow through the device in the opposite direction when the valve is closed. Thus, while the leaflet substantially prevents fluid flow in the second, opposite direction, the device includes an opening that allows some flow of fluid in this direction. Allowing such flow, retrograde flow, lessens pooling of fluid around the device when the leaflet is in the closed, or second, position. This is expected to prevent pooling of blood around the device, which may prevent formation of thrombus and increase the overall acceptance of the device by a host.

The opening can be defined entirely by the leaflet, or by at least a portion of an edge of the leaflet and a portion of the support frame. In either embodiment, a liner can be placed on at least a portion of the opening. The liner provides structural integrity to the perimeter of the opening, and may define structural features that maintain a distance between the leaflet and a wall of the vessel. Further, the liner may define structural features that facilitate fluid flow through the opening in the second, opposite direction.

The opening is advantageously dimensioned to permit sufficient retrograde flow to achieve the desired effect without destroying the valve function of the device. In the venous valve embodiments, the total open area of the opening can be compared to the total cross-sectional area of the vessel lumen. In some embodiments, the total open area of the opening is less than the total cross-sectional area of the vessel at a desired point of treatment. In other embodiments, the total open area of the opening is less than half of the total cross-sectional area of the vessel.

The device can include more than one opening that permits a controlled amount of retrograde flow through the device.

A more detailed explanation of the invention is provided by the attached drawings and detailed description, which illustrate exemplary embodiments of the invention.

DETAILED DESCRIPTION OF EXEMPLARY EMBODIMENTS OF THE INVENTION

The following provides a detailed description of exemplary embodiments of the invention. The description is not intended to limit the invention in any manner, but rather serves to enable those skilled in the art to make and use the invention.

A medical device according to the invention provides a valve for regulating fluid flow through a body vessel. The device includes a support frame and at least one valve leaflet. The leaflet provides a means for regulating fluid flow through the body vessel, and the support frame provides a surface to which the valve leaflet is attached.

A wide variety of support frames are known in the medical technology arts, and any suitable support frame can be utilized. The only requirement is that the support frame provide a surface to which the valve leaflet can be attached and function as described herein.

As described below, the support frame advantageously has radially compressed and radially expanded configurations. Such a support frame can be implanted at a point of treatment within a body vessel by minimally invasive techniques, such as delivery and deployment with an intravascular catheter. The support frame can optionally provide additional function to the medical device. For example, the support frame can provide a stenting function, i.e., exert a radially outward force on the interior wall of a vessel in which the medical device is implanted. By including a support frame that exerts such a force, a medical device according to the invention can provide both a stenting and a valving function at a point of treatment within a body vessel.

The stent art provides numerous support frames acceptable for use in the present invention, and any suitable stent can be used as the support frame. The specific support frame chosen will depend on numerous factors, including the body vessel in which the medical device is being implanted, the axial length of the treatment site within the vessel, the number of valves desired in the medical device, the inner diameter of the vessel, the delivery method for placing the medical device, and other considerations. Those skilled in the art can determine an appropriate support frame based on these and other considerations.

The support frame can be self-expandable or balloon expandable. The structural characteristics of both of these types of support frames are known in the art, and are not detailed herein. Each type of support frame has advantages and for any given application, one type may be more desirable than the other based on a variety of considerations. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, medical devices according to the invention intended for implantation in the peripheral vasculature, such as prosthetic venous valves, advantageously include a self-expandable support frame. These support frames, as is known in the art, are generally more flexible than balloon-expandable support frames following deployment.

Suitable support frames can be made from a variety of materials and need only be biocompatible or able to be made biocompatible. Examples of suitable materials include, without limitation, stainless steel, nickel titanium (NiTi) alloys, e.g., nitinol, other shape memory and/or superelastic materials, polymers, and composite materials. Also, resorbable and bioremodellable materials can be used. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Stainless steel and nitinol are currently considered desirable materials for use in the support frame due at least to their biocompatibility, shapeability, and well-characterized nature.

Suitable support frames can also have a variety of shapes and configurations, including braided strands, helically wound strands, ring members, consecutively attached ring members, zig-zag members, tubular members, and frames cut from solid tubes.

Examples of suitable support frames for use in medical devices according to the invention include those described in U.S. Pat. Nos. 6,464,720 to Boatman et al. for a RADIALLY EXPANDABLE STENT; 6,231,598 to Berry et al. for a RADIALLY EXPANDABLE STENT; 6,299,635 to Frantzen for a RADIALLY EXPANDABLE NON-AXIALLY CONTRACTING SURGICAL STENT; 4,580,568 to Gianturco for a PERCUTANEOUS ENDOVASCULAR STENT AND METHOD FOR INSERTION THEREOF; and published application for U.S. Pat. No. 20010039450 to Pavcnik et al. for an IMPLANTABLE VASCULAR DEVICE, each of which is hereby incorporated by reference in its entirety for the purpose of describing suitable support frames for use in medical devices according to the invention.

FIGS. 1, 1A, 2, and 3 illustrate a suitable support frame 10 for use in a medical device according to the invention. Support frame 10 is described in detail in U.S. Pat. No. 6,508,833 to Pavcnik et al. for a MULTIPLE-SIDED INTRALUMINAL MEDICAL DEVICE, which is hereby incorporated by reference in its entirety for the purpose of describing suitable support frames for use in medical devices according to the invention. This support frame 10 is described briefly herein as an example of a suitable support frame for use in medical devices according to the invention.

Figure 1:
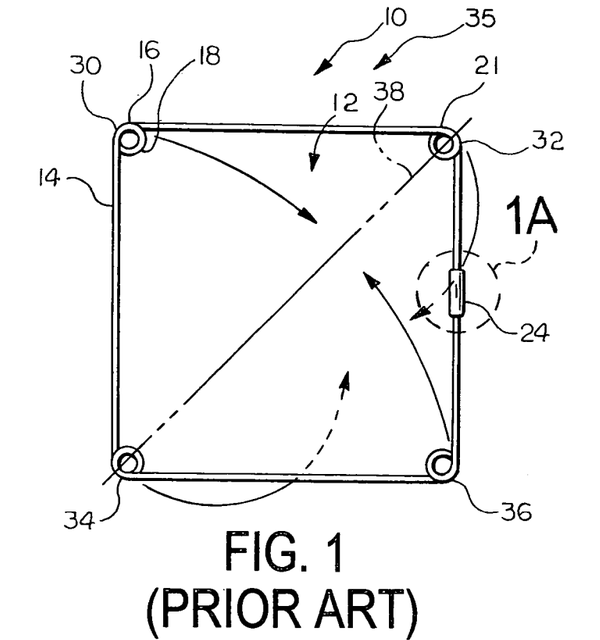
FIG. 1 is a top view of a support frame for use in medical devices according to the present invention.
Figure 1A:
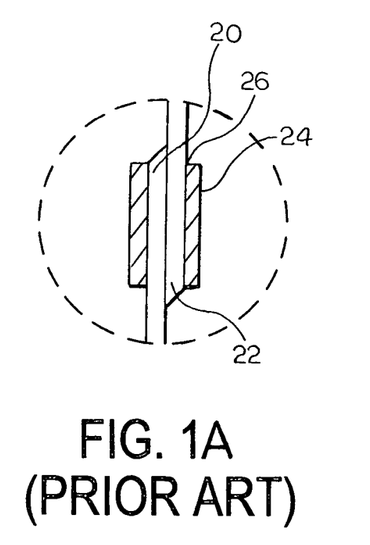
FIG. 1A is an enlarged partially sectioned view of the support frame illustrated in FIG. 1.

The support frame 10 is made of resilient material, preferably metal wire formed from stainless steel or a superelastic alloy, such as nitinol. While round wire is depicted in the figures, other types, such as flat, square, triangular, D-shaped, and delta-shaped wire, may be used to form the frame 10. In the illustrated embodiment, the frame 10 comprises a closed circumference 12 of a single piece of material that is formed into a device having a plurality of sides 14 interconnected by a series of bends 16. The illustrated embodiment includes four sides 14 of approximately equal length. Alternative embodiments include frames with sides of different lengths, and frames of any polygonal shape, such as pentagon, hexagon, and octagon shapes.

In the embodiment illustrated in FIGS. 1, 1A, 2 and 3, the bends 16 interconnecting sides 14 comprise a coil 18 of approximately one and a quarter turns. The coil 18 produces superior bending fatigue characteristics over those of a simple bend in support frames formed of stainless steel and most other standard materials. A simple bend, such as a substantially orthogonal bend, may be more appropriate, however, if the frame is formed of nitinol or other superelastic alloy, because the formation of certain types of bends, such as coil 18, may actually decrease fatigue life of a superelastic material. The specific structure chosen for bend 16 should be one that minimizes bending fatigue for the material of which the support frame 10 is formed. Alternative bend embodiments include outward-projecting fillets and inward-projecting fillets comprising a series of curves. Fillets are well known in the stent art as a means for reducing stresses in bends.

The cross-sectional diameter of the wire selected will depend on the size of the medical device and the application. Wire that is too stiff can damage the vessel, not conform well to the vessel wall, and increase the profile of the device when loaded in a delivery system prior to deployment. Wire that is not sufficiently stiff may not allow the valve leaflet to function as desired.

The single piece of material comprising the frame 10 is formed into the closed circumference 12 by securing the first and second ends 20, 22 with an attachment mechanism 24, such as a metal cannula. The ends 20, 22 are inserted into the cannula 24 and secured with a bonding element 26, such as solder, an adhesive, or other suitable bonding element. Also, a mechanical bond can be formed between the ends 20, 22 and attachment mechanism 24 by crimping, deformation of adjacent elements, or any other suitable technique. Also, the ends 20, 22 can be joined directly to each other without addition of an attachment mechanism, such as by soldering, welding, or other suitable methods to join material. Also alternatively, the frame 10 can be fabricated as a single piece of material by stamping or cutting a pattern from a sheet such as with a laser, fabricating from a mold, or some similar method of producing a unitary frame.

FIG. 1 illustrates the frame 10 in a first configuration 35 in which all corners 30, 32, 34, 36 of the polygon and each of the sides 14 generally lie within a single flat plane. To resiliently reshape the frame 10 into a second configuration 45, shown in FIG. 2, the frame 10 is folded twice, first along one diagonal axis 38 with opposite bends 30, 36 being brought into closer proximity with respect to each other, followed by opposite bends 32, 34 being folded toward each other and brought into closer proximity. The second configuration 45 has two opposite bends 30, 36 oriented at the first end 40 of the frame 10, while the other opposite bends 32, 34 are oriented at the second end 42 of the frame 10 and rotated approximately 90° with respect to bends 30, 36 when viewed in cross-section.

Figure 2:
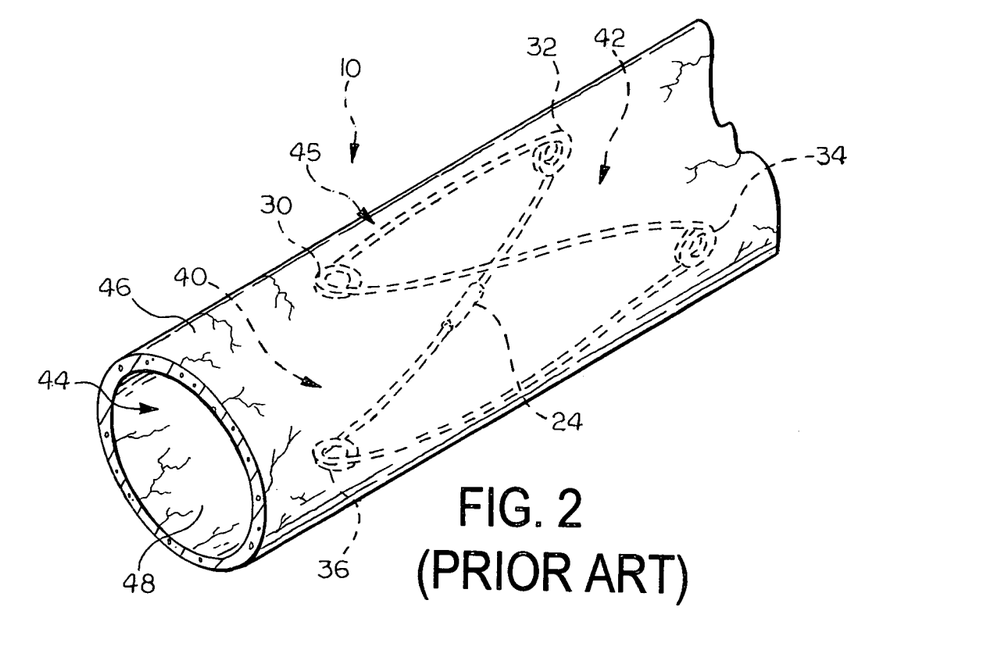
FIG. 2 is a perspective view of the support frame illustrated in FIG. 1 deployed within a body vessel.

When deployed in a lumen 44 of a vessel 46, as illustrated in FIG. 2, the support frame 10 in the second configuration 45 exerts a radially outward force on the interior wall 48 of the vessel 46. The bending stresses introduced to the frame 10 by the first and second folds required to form the second configuration 45 apply force radially outward against the vessel wall 48 to hold the frame 10 in place and prevent vessel closure. Absent any significant plastic deformation occurring during folding and deployment, the second configuration 45, when not in the vessel 46 or subject to other constraining means, will at least partially return to the first configuration 35, although some deformation can occur depending on the material used. It is also possible to plastically deform the frame 10 into the second configuration 45, such that it does not unfold when restraint is removed. This might be particularly desirable if the device is made from nitinol or a superelastic alloy.

Figure 3:
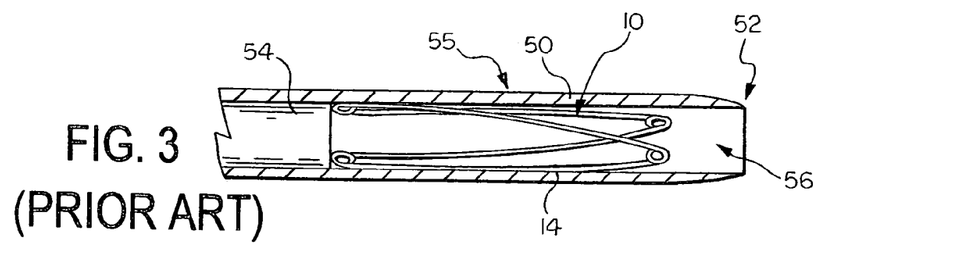
FIG. 3 is a partially sectioned view of the support frame illustrated in FIG. 1 within a delivery device.

As illustrated in FIG. 3, the frame 10 is formed into a third configuration 55 for loading into a delivery device 50, such as a catheter. In the third configuration 55, adjacent sides 14a, 14b are generally beside each other in close proximity and extend generally along the same axis. To advance and deploy the support frame 10 from the distal end 52 of the delivery device 50, a pusher 54 is placed into the catheter lumen 56. When the frame 10 is fully deployed within a vessel, it assumes the second configuration 45 as illustrated in FIG. 2. The sides 14 of the frame 10, being made of resilient material, conform to the shape of the vessel wall 48 such that when viewed on end, the frame 10 has a generally circular appearance when deployed in a round vessel. As a result, sides 14 are arcuate or slightly bowed out to better conform to the vessel wall 48.

Figure 4:
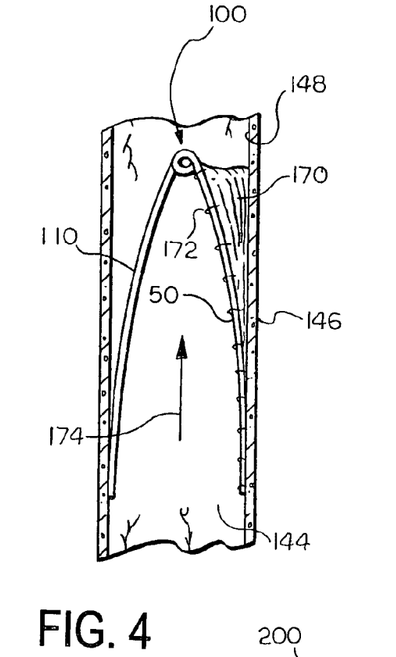
FIG. 4 is a partially sectioned view of a body vessel containing a medical device according to a first embodiment of the invention.
Figure 5:
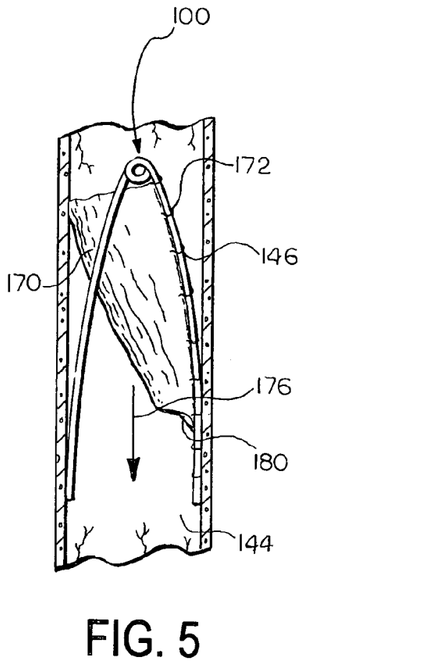
FIG. 5 is a partially sectioned view of a body vessel containing the medical device illustrated in FIG. 4 in a closed position.

FIGS. 4 and 5 illustrate a medical device 100 according to a first embodiment of the invention. The device 100 includes a support frame 110 and a valve leaflet 170 attached to the support frame 110. In this embodiment, the support frame 110 is the support frame 10 illustrated in FIGS. 1, 1A, 2, and 3.

The valve leaflet 170 comprises a section of material, such as a sheet, that is attached to the support frame 110. The valve leaflet 170 can be formed of any suitable material, and need only be biocompatible or be able to be made biocompatible. The material can advantageously be formed of a flexible material. Examples of suitable materials for the valve leaflet 170 include natural materials, synthetic materials, and combinations of natural and synthetic materials. Examples of suitable natural materials include extracellular matrix (ECM) materials, such as small intestine submucosa (SIS), and other bioremodellable materials, such as bovine pericardium. Other examples of ECM materials that can be used in the prosthetic valves of the invention include stomach submucosa, liver basement membrane, urinary bladder submucosa, tissue mucosa, and dura mater. Examples of suitable synthetic materials include polymeric materials, such as expanded polytetrafluoroethylene and polyurethane. ECM materials are particularly well-suited materials for use in the valve leaflet 170, at least because of their abilities to remodel and become incorporated into adjacent tissues. These materials can provide a scaffold onto which cellular in-growth can occur, eventually allowing the material to remodel into a structure of host cells.

The valve leaflet 170 is attached to the support frame 110 in any suitable manner. As illustrated in FIGS. 4 and 5, sutures 172 can be used for the attachment. Alternatively, the valve leaflet 170 can be attached to the support frame 110 by other means for attaching, such as adhesives, heat sealing, tissue welding, weaving, cross-linking, or any other suitable means for attaching. The specific means for attaching chosen will depend at least upon the materials used in the valve leaflet 170 and the support frame 110.

The valve leaflet 170 is moveable between first and second positions when the device 100 is placed within a body vessel 146. In the first position, illustrated in FIG. 4, the leaflet 170 permits fluid flow in a first direction, represented by arrow 174, to flow through the device 100. The pressure created by the flow of fluid exerts a force on one face of the leaflet 170, forcing it toward vessel wall 148. In the second position, illustrated in FIG. 5, the leaflet 170 substantially prevents fluid flow in a second, opposite direction, represented by arrow 176 from flowing through the device 100. The valve leaflet 170 moves to the second position when a pressure change and/or reversal of flow direction exerts a force on an opposite face of the leaflet 170 and forces the leaflet 170 away from the vessel wall 148 and across the lumen 144 of the vessel 146. The first position of the valve leaflet 170 can be considered an open position, and the second position can be considered a closed position. By moving between these two positions, the leaflet 170 provides a valving function to the medical device 100, allowing it to regulate fluid flow through the medical device 100, and consequently the vessel 144.

The medical device 100 illustrated in FIGS. 4 and 5 is a prosthetic valve, and can be used as a prosthetic venous valve. In this capacity, the device 100 is placed in a vein to regulate the flow of blood through the vein. It is believed that the valve leaflet 170 moves to the first position, illustrated in FIG. 4, during systole in which the heart forces blood through the vein in the first direction 174. During diastole, the leaflet 170 moves to the second position, illustrated in FIG. 5, to substantially prevent fluid flow in the second, opposite direction 176. It is believed that a pressure change and reversal of flow direction occurs during the change from systole to diastole, and the valve leaflet 170 changes position in response to these changes. Flow in the second opposite direction 176 is commonly referred to as retrograde flow.

The leaflet 170 substantially, but not entirely, prevents fluid flow in the second, opposite direction 176 for at least two reasons. First, as the valve leaflet 170 moves from the first position to the second position, a time period passes before the valve leaflet is in the second position, and some retrograde flow may pass through the device 100 during this time. Second, the medical device 100 includes an opening 180 that permits a controlled amount of fluid flow to pass through the medical device 100 in the second, opposite direction 176.

The opening 180 provides a passageway through which a controlled amount of retrograde flow 176 can pass when the leaflet 170 is in the second position. The retrograde flow 176 passing through the opening 180 may facilitate closure of the valve by allowing some of the retrograde flow 176 to continue moving past the leaflet 170. Also, the opening 180 provides an escape through which blood can move to prevent pooling during periods in which the valve leaflet 170 is in the second, or closed, position.

The retrograde flow 176 that passes through the opening 180 when the valve leaflet 170 is in the second position is controlled by the overall dimensions and configuration of the opening 180. A larger opening 180 allows a greater amount of retrograde flow 176 to pass through the medical device 100, while a relatively smaller opening 180 will allow a relatively lesser amount of retrograde flow 176 to pass. The dimensions and configuration of the opening 180 can be optimized based upon the vessel in which the device 100 is placed. The size and configuration selected will depend on several factors, including the vessel size, typical flow volumes and rates, and others. The opening 180 is advantageously sized to allow a desired amount of retrograde flow pass through the opening 180 during periods of retrograde flow 176. The opening 180 should be small enough, though, to still allow the leaflet 170 to substantially prevent retrograde flow 176 to pass through the device while in the second position. Thus, the opening 180 is advantageously sized so as to not allow a majority of retrograde flow 176 to pass through the opening 180. Thus, the total open area of the opening 180 is, at a maximum, less than the cross-sectional area of the vessel lumen 144. As used herein, the term "total open area", in relation to the opening, refers to the total area of the opening 180 when the entire perimeter of the opening 180 lies in the same plane.

The opening 180 can be advantageously sized to mimic the degree of retrograde flow—the leakiness—that is present in a natural valve located at the point of treatment in the body vessel. Accordingly, the dimensions of the opening 180 can be determined and optimized based upon the vessel in which the device 100 is to be placed. For venous valve applications, the total open area of the opening 180 is advantageously less than about 50% of the cross-sectional area of the vessel at the intended point of deployment. More advantageously, the total open area of the opening 180 is less than about 25% of the total cross-sectional area of the vessel at the intended point of deployment. In one example, a device is configured for placement in a vessel having a total cross-sectional area of about 50 mm². In this example, the opening has a total open area of about 20 mm². Also for venous valve applications, a circular opening with a diameter of between about 0.5 and about 3.0 mm has been found to be suitable. In a specific venous valve example, a circular opening with a diameter of about 1 mm has been found to be suitable. In another specific venous valve example, a circular opening with a diameter of about 2 mm has been found to be suitable.

Figure 6:
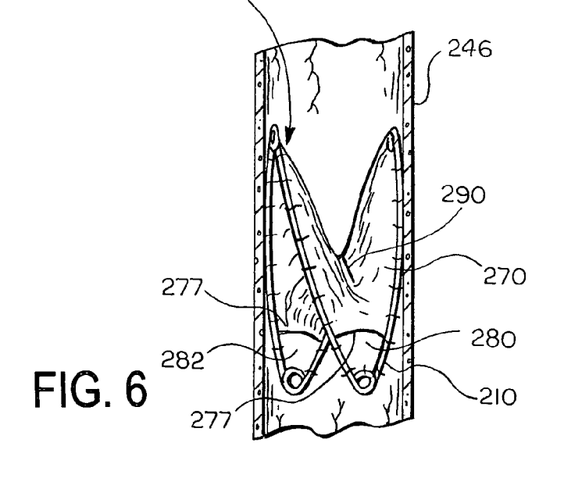
FIG. 6 is a partially sectioned view of a body vessel containing a medical device according to a second embodiment of the invention.

FIG. 6 illustrates a medical device 200 according to a second embodiment of the invention. In this embodiment, the leaflet 270 spans the entire support frame 210, and includes a slit 290 that defines an aperture in the leaflet 270. The leaflet 270 opens and closes the slit 290 to permit flow in a first direction and substantially prevent flow in a second, opposite direction, i.e., retrograde flow, by moving the slit from a first open position to a second closed position. The slit 290 can be oriented relative to the frame 210 as shown, or in any other suitable orientation.

In this embodiment, the medical device 200 includes multiple openings 280, 282 for allowing a controlled amount of retrograde flow to pass through the device 200 when the slit 290 is in the second, closed position. Each of the openings 280, 282 is as described above for the first embodiment and the total cumulative open area of the openings 280, 282 is, at a maximum, less than the cross-sectional area of the vessel 246 at the intended point of deployment. Also in this embodiment, an edge 277 of the leaflet 270 and a portion of the support frame 210 cooperatively define each opening 280, 282. This configuration is particularly desirable in devices with leaflets formed of bioremodellable materials, such as ECM materials, or other materials that can become adhered to or incorporated into a vessel wall 246 following repeated and/or prolonged contact between the leaflet 270 and wall 246. In these embodiments, the opening reduces the overall surface area of the valve leaflet that contacts the vessel wall as the valve leaflet moves between the first and second positions.

It is believed that this reduction in surface area may reduce or eliminate the possibility that the valve leaflet would become adhered to or incorporated into the vessel wall. Also, this positioning of the opening relative to the support frame prevents stress that might be placed on the valve leaflet during movement of the resilient support frame if the opening were not present. This may prevent damage to the valve leaflet. Thus, in the embodiment illustrated in FIG. 6, each of the openings 280, 282 permits retrograde flow to pass through the medical device 200 when the slit 290 is in the closed position, and protects the leaflet 270 by spacing it away from the vessel wall 246. It is understood that, while two openings 280, 282 are illustrated in this embodiment, the device 200 could include only a single opening, or more than two openings.

Figure 7:
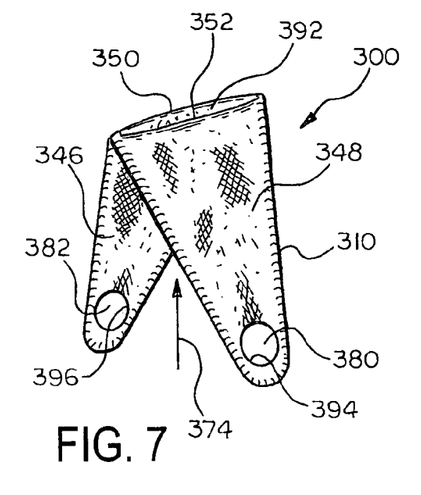
FIG. 7 is a perspective view of a medical device according to a third embodiment of the invention.

FIG. 7 illustrates a medical device 300 according to a third embodiment of the invention. In this embodiment, the device 300 includes two leaflets 346, 348 that are attached to the support frame 310. Each leaflet 346, 348 has a free edge 350, 352 that is not attached to the support frame 310. The free edges 350, 352 cooperatively define valve orifice 392. The leaflets 346, 348 are both movable between first and second positions. In the first position, illustrated in FIG. 7, the orifice 392 is open and allows fluid flow through the device 300 in a first direction, represented by arrow 374. In the second position, the free edges 350, 352 of leaflets 346, 348 come together to close the orifice 392 and substantially prevent fluid flow through the device in a second, opposite direction.

Each leaflet 346, 348 defines an opening 380, 382 that allows a controlled amount of retrograde flow to pass through the medical device 300 when the valve orifice 392 is closed. In this embodiment, each of the openings 380, 382 is defined entirely by the respective leaflet 346, 348. Thus, one or more edges 394, 396 of the leaflets 346, 348 define each of the openings 380, 382.

Figure 8:
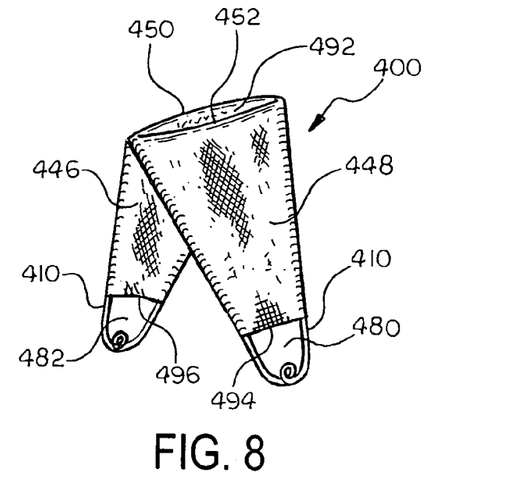
FIG. 8 is a perspective view of a medical device according to a fourth embodiment of the invention.

FIG. 8 illustrates a medical device 400 according to a fourth embodiment of the invention. The device 400 of this embodiment is similar to the device illustrated in FIG. 7, except that each opening 480, 482 is partially defined by an edge 494, 496 of a leaflet 446, 448 and a portion of the support frame 410. As described above, this configuration of the openings 480, 482 may be advantageous if the valve leaflets 446, 448 are formed of a bioremodellable material or other material that can become adhered to and/or incorporated into a vessel wall following repeated and/or prolonged contact between the valve leaflets 446, 448 and the vessel wall. Similar to the embodiment illustrated in FIG. 7, free edges 450, 452 of leaflets 446, 448 define valve orifice 492 which opens and closes to regulate fluid flow through the device 400.

Figure 9:
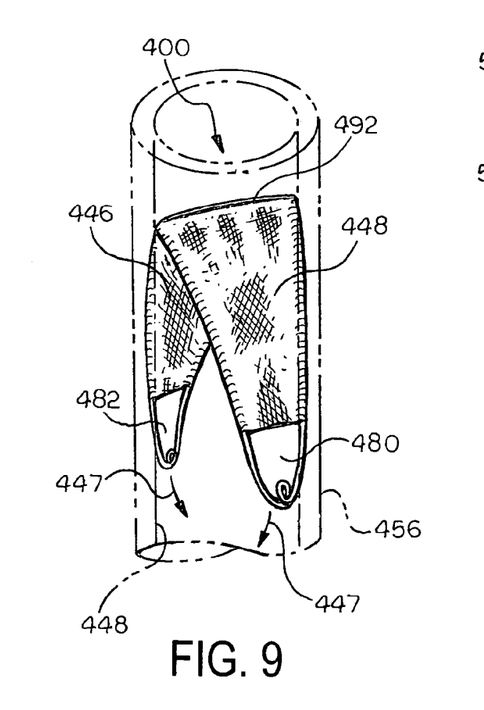
FIG. 9 is a perspective view of a body vessel containing the medical device illustrated in FIG. 8.

FIG. 9 illustrates the device 400 of FIG. 8 inside a body vessel 456. In FIG. 9, the valve leaflets 446, 448 are in the second position in which the valve orifice 492 is closed. Thus, the device 400 as illustrated is in position to substantially prevent fluid flow in the second, opposite direction. The openings 480, 482 permit a controlled amount of retrograde flow 447 to flow through the device 440 while the valve orifice 492 is closed. Also, the openings 480, 482 are positioned on the device 400 such that the leaflets 446, 448 are protected from substantial contact with the interior wall 448 of the vessel 456.

Figure 10:
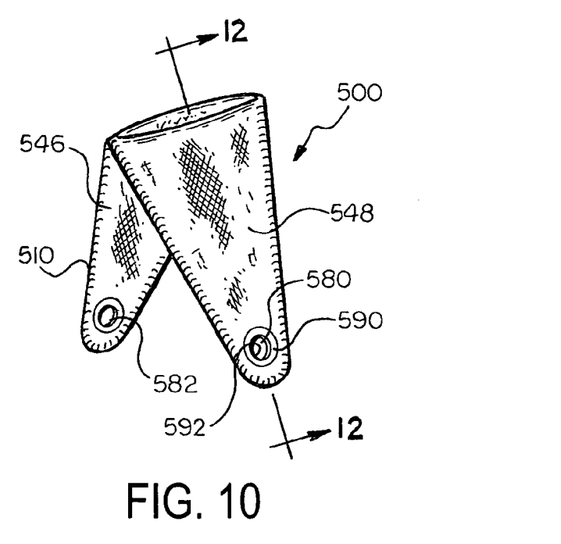
FIG. 10 is a perspective view of a medical device according to a fifth embodiment of the invention.
Figure 11:
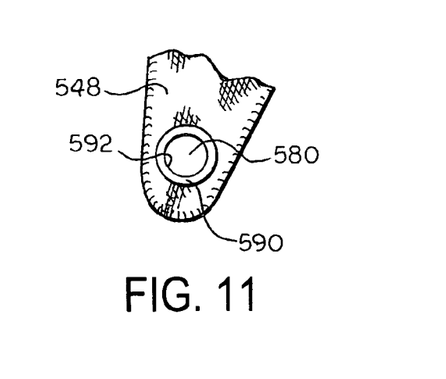
FIG. 11 is an enlarged partial view of a portion of the medical device illustrated in FIG. 10.
Figure 12:
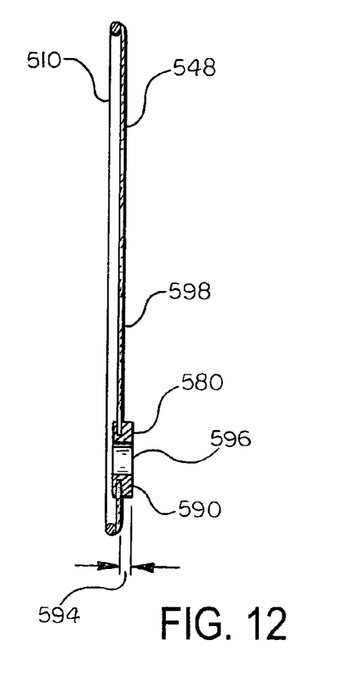
FIG. 12 is a sectional view of the medical device illustrated in FIG. 10 taken along line 12-12.

FIGS. 10, 11 and 12 illustrate a medical device 500 according to a fifth embodiment of the invention. In this embodiment, the device 500 includes a liner 590 secured to the perimeter 592 of the opening 580. As best illustrated in FIG. 12, the liner 590 has a thickness 594 that spaces a surface 596 of the liner 590 from a surface 598 of the leaflet 548. When the device 500 is deployed in a vessel, the surface 596 of the liner 590 is the outermost surface of that portion of the device 500 with respect to the interior of the vessel. This configuration protects the respective valve leaflet 548 from the vessel wall.

The liner 590 can be made from a different material than the leaflets 546, 548 on which it is disposed, or comprises a portion of the leaflets 546, 548 that has been treated in a manner that prevents or reduces adhesion to and/or incorporation into the vessel wall as compared to the untreated portions of the valve leaflets 546, 548. The liner 590 is advantageously formed of a suitable biocompatible material, such as an appropriate plastic or metal, and is attached to the valve leaflets 546, 548 by appropriate means for attaching such a material to the material of the leaflets 546, 548, such as crimping, stitching, annealment, or other suitable means for attaching. Advantageously, as illustrated in FIGS. 10, 11 and 12, the liner 590 comprises a grommet attached to the perimeter 592 of the openings 580, 582.

Figure 13:
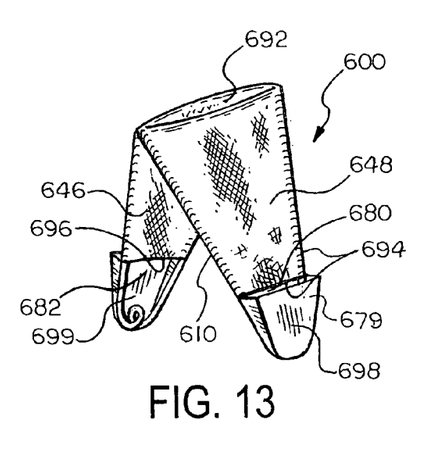
FIG. 13 is a perspective view of a medical device according to a sixth embodiment of the invention.
Figure 14:
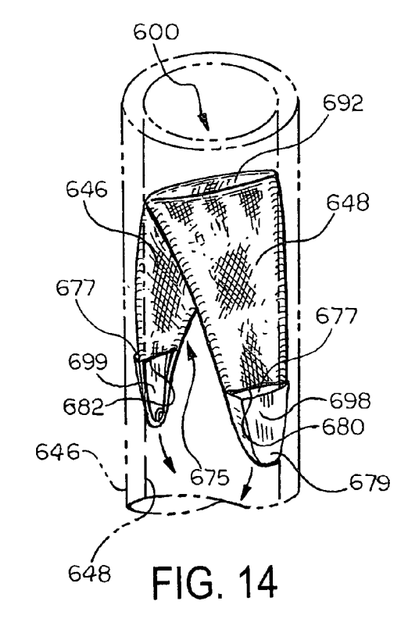
FIG. 14 is a perspective view of a body vessel containing the medical device illustrated in FIG. 13.

FIGS. 13 and 14 illustrate a medical device 600 according to a sixth embodiment of the invention. This embodiment is similar to the embodiment illustrated in FIG. 8, except as described below. The medical device 600 includes first 698 and second 699 liners disposed adjacent first 680 and second 682 openings that allow a controlled amount of retrograde flow through the device 600 when the valve orifice 692 is in a closed position. The opening 680 is defined by an edge 694 of the leaflet 648 and a portion of the support frame 610, and the second opening 682 is defined by an edge 696 of the leaflet 646 and another portion of the support frame 610.

The liners 698, 699 are attached to the support frame 610. The liner 698 has a first surface 679 that extends at an angle to the support frame 610 and substantially parallel to the vessel wall following deployment of the medical device 600. Also, the liner 698 defines a passageway 677 through which retrograde flow can proceed into the opening 680 and, ultimately, through the medical device 600. The liner 698 can be attached to the support frame 610 in a manner that creates an overlap region that represents a length along an axis of the medical device 600 in which the liner 698 overlaps the valve leaflet 648. The second liner 699 advantageously has the same structure, and is attached to the support frame 610 in the same manner, as the first liner 698.

Figure 15:
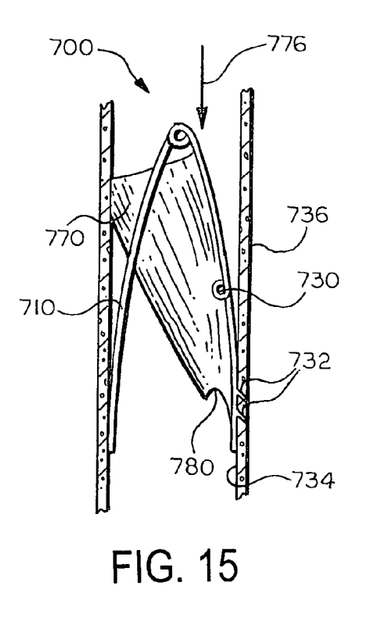
FIG. 15 is a partially sectioned view of a body vessel containing a medical device according to a seventh embodiment of the invention.

FIG. 15 illustrates a medical device 700 according to a seventh embodiment of the invention. This embodiment is similar to the embodiment illustrated in FIGS. 4 and 5, except as detailed below. Thus, the medical device 700 includes a support frame 710 and a valve leaflet 770 attached to the support frame 710. An opening 780 in the valve leaflet 770 allows a controlled amount of retrograde flow, represented by arrow 776, to flow through the medical device 700 when the valve leaflet 770 is in a second, or closed, position.

In this embodiment, the support frame 710 includes a hinge 730. The hinge 730 is a structural feature of the support frame 710, such as the illustrated eyelet, that allows the support frame to temporarily bend. Temporary bending of the support frame 710 is expected to allow the support frame to adjust to different loads placed on the support frame 710 as fluid flow through the device 700 changes direction. For example, the support frame 710 may undergo a change in radial or other load when the flow direction changes. Also in this embodiment, the support frame 710 includes barbs 732 to secure the device 700 to the interior wall 734 of the vessel 736.

Figure 16:
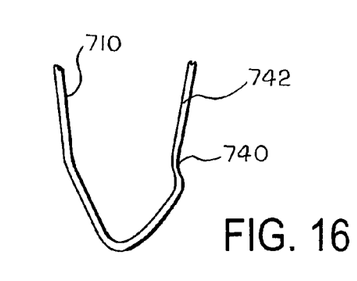
FIG. 16 is a partial top view of a support frame for use in medical devices according to the present invention.

The hinge 730 can be any suitable structural feature that allows for temporary bending of the frame 710, and the eyelet is but one illustrative example. As illustrated in FIG. 16, a structurally weaker section 740 of the frame 710 can be used at a position on the support frame 710 where bending is desirable, such as a position that will be adjacent the opening 780 in the finished medical device 700. The structurally weaker section 740 is able to bend to a greater degree than a relatively stronger section 742. The structurally weaker section 740 can be weaker than the stronger section 742 due to a different geometry, such as a circular cross-sectional shape as opposed to a square cross-sectional shape, or can comprise a thinner or narrower section of material than that in the relatively stronger section 742.

Figure 17A:
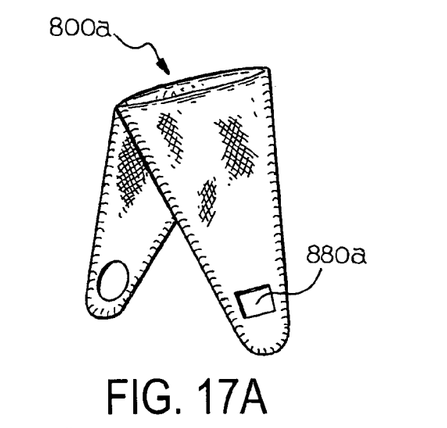
FIGS. 17A, 17B, 17C, and 17D are perspective views of medical devices according to the invention.
Figure 17B:
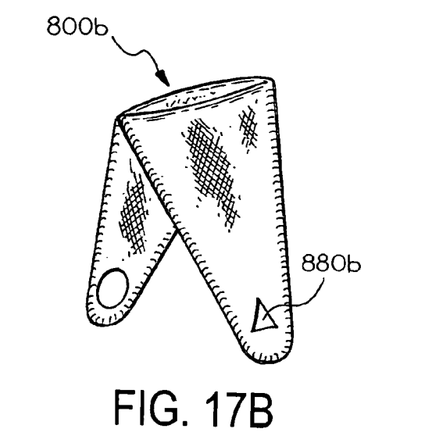
Figure 17C:
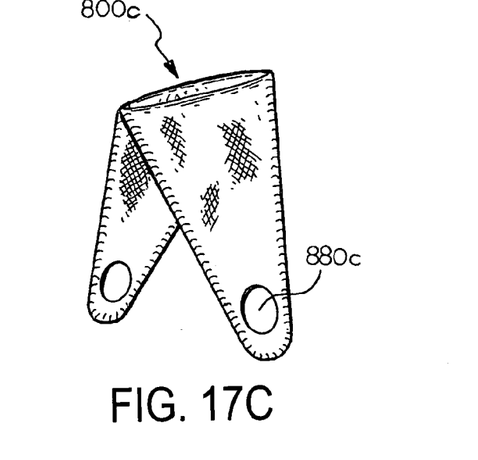
Figure 17D:
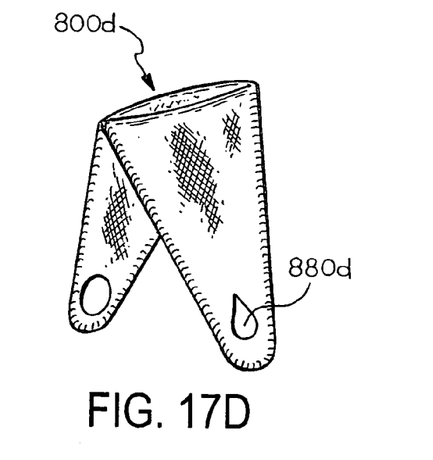

While the opening for allowing a controlled amount of retrograde flow to flow through the medical device is depicted as a circular or a partial circular opening in some of the figures, it is understood that the opening can have any suitable shape, including square, triangular, ovoid, and teardrop shapes. FIGS. 17A, 17B, 17C and 17D illustrate medical devices 800a, 800b, 800c, and 800d, respectively, that include openings 880a, 880b, 880c, and 800d, respectively, having various suitable shapes. Specific examples of suitable shapes include a substantially square opening 880a (FIG. 17A), a substantially triangular opening 880b (FIG. 17B), a substantially ovoid opening 880c (FIG. 17C), and a teardrop-shaped opening 880d (FIG. 17D). The actual shape chosen for the opening will depend on various factors, including the desired quantity of retrograde flow, the size and configuration of the leaflet(s) of the medical device, and the size and configuration of the vessel in which the medical device will be employed.

Figure 18:
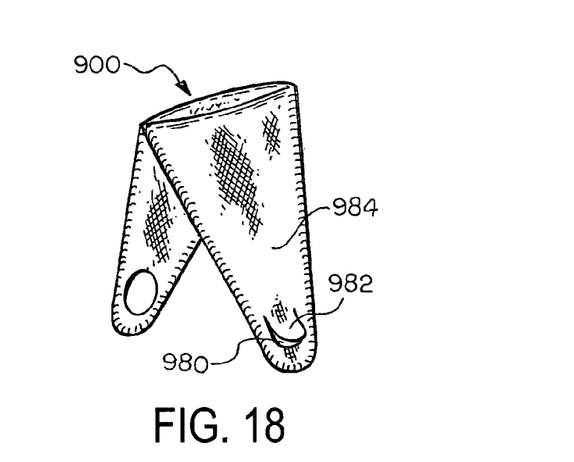
FIG. 18 is a perspective view of a medical device according to another embodiment of the invention.
Figure 19A:
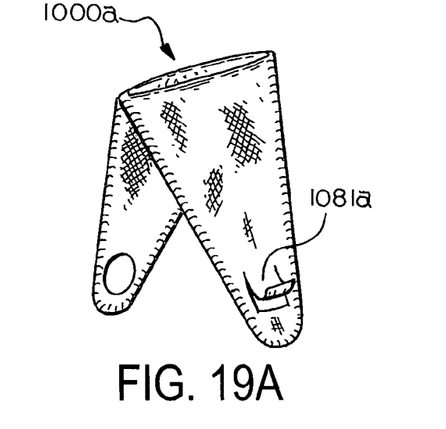
FIGS. 19A, 19B, 19C, 19D, 19E, and 19F are perspective views of medical devices according to the invention.
Figure 19B:
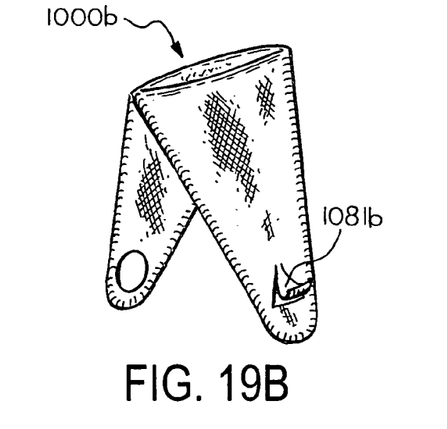
Figure 19C:
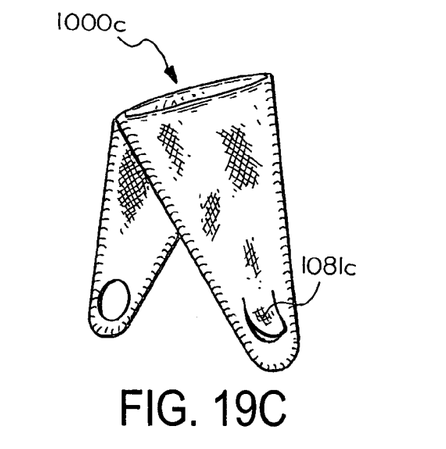
Figure 19D:
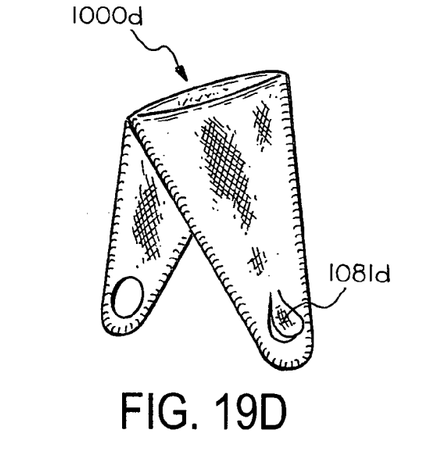
Figure 19E:
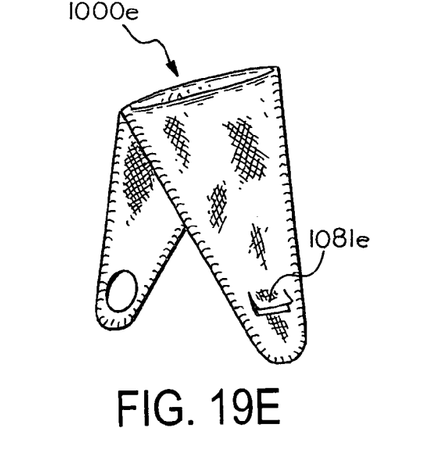
Figure 19F:
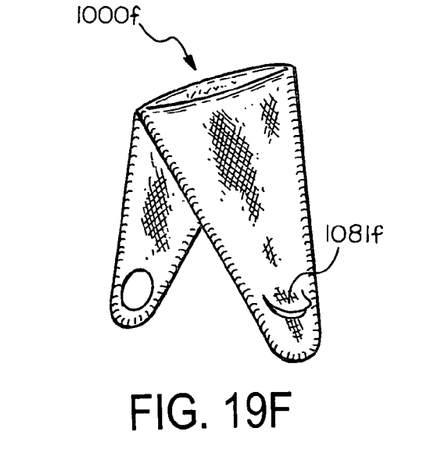

The opening for allowing a controlled amount of retrograde flow through the medical device can be substantially covered by a flap created in a leaflet. A flap configuration may allow retrograde flow to proceed through the opening, and minimize or prevent any antegrade flow from proceeding through the opening. As used herein, the term "flap" refers to a section of material that is connected to or integrally formed with adjacent material at one side or end, but is free of adjacent material at another side or end. The flap is a moveable section of material that is adjacent the opening. As the flap moves, it is able to temporarily and substantially close the opening. FIG. 18 illustrates a medical device 900 that includes an opening 980 defined by a flap 982 formed in the leaflet 984. FIGS. 19A, 19B, 19C, 19D, 19E, and 19F illustrate medical devices 1000a, 1000b, 1000c, 1000d, 1000e, and 1000f, respectively, that include flaps 1081a, 1081b, 1081c, 1081d, 1081e, 1081f, respectfully, of various suitable shapes. Specific examples of suitable shapes include a partial square flap 1081a (FIG. 19A), a partial triangular flap 1081b (FIG. 19B), a partial ovoid flap 1081c (FIG. 19C), and a partial teardrop-shaped flap 1081d (FIG. 19D). FIG. 19E illustrates a partial rectangular flap 1081e and FIG. 19F illustrates a crescent-shaped flap 1081f. The actual shape chosen for the flap will depend on various factors, including the desired quantity of retrograde flow, the size and configuration of the leaflet(s) of the medical device, the desired ability of the flap to close, and the size and configuration of the vessel in which the medical device will be employed.

Figure 20A:
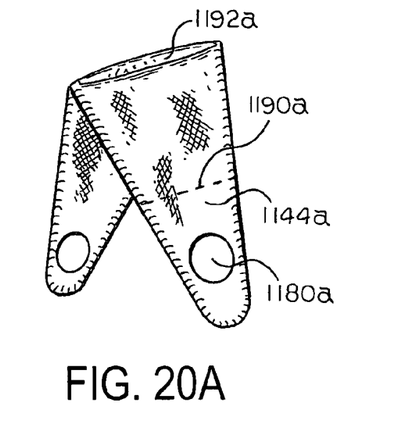
FIGS. 20A, 20B, 20C, and 20D are perspective views of medical devices according to the invention.
Figure 20B:
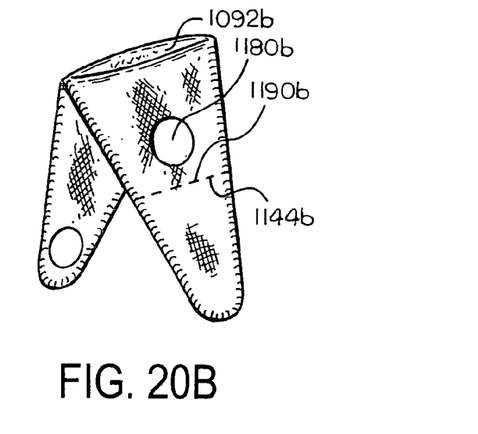
Figure 20C:
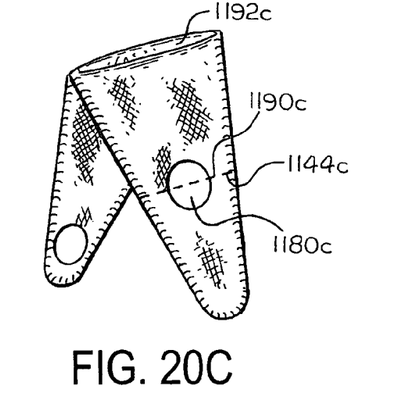
Figure 20D:
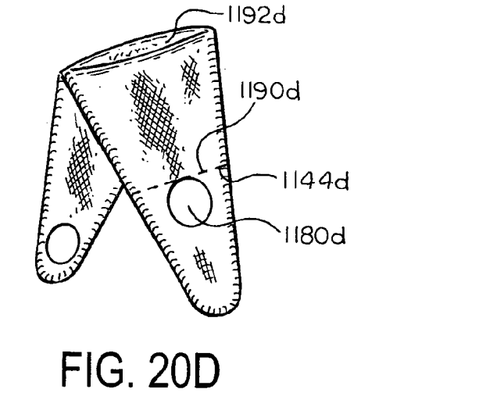

The opening that permits a controlled amount of retrograde flow to pass through the medical device can be positioned at various locations on the leaflet. The position on the leaflet may affect the quantity of retrograde flow that proceeds through the opening, the flow dynamics of retrograde flow that proceeds through the opening, and the quantity of any antegrade flow that might proceed through the opening. As illustrated in FIG. 20A, the opening 1180a can be positioned distal to a centerline 1190a of the leaflet 1144a, relative to the valve orifice 1192a. The centerline 1190a is an imaginary line that proceeds through the vertical midpoint of the valve leaflet 1144a. As illustrated in FIG. 20B, the opening 1180b can be positioned between a centerline 1190b and the valve 1192b. FIG. 20C illustrates an embodiment in which a centerline 1190d proceeds through the opening 1180c. Also, the centerline 1144d can comprise a portion of the perimeter of the opening 1180d, as illustrated in FIG. 20D. If a flap embodiment is used, the flap can be positioned on the leaflet in a similar manner. The exact position chosen for the opening and flap, if utilized, will depend on various factors, including the desired flow dynamics of retrograde flow passing through the opening.

In all embodiments of the invention, the opening for allowing a controlled amount of retrograde flow through the medical device can be formed by any suitable technique, including cutting and punching. The flap, if used, can also be formed by these and other suitable techniques. Furthermore, the opening can be formed prior to or following attachment of the valve leaflet to the support frame.

Figures 21, 22, 23:
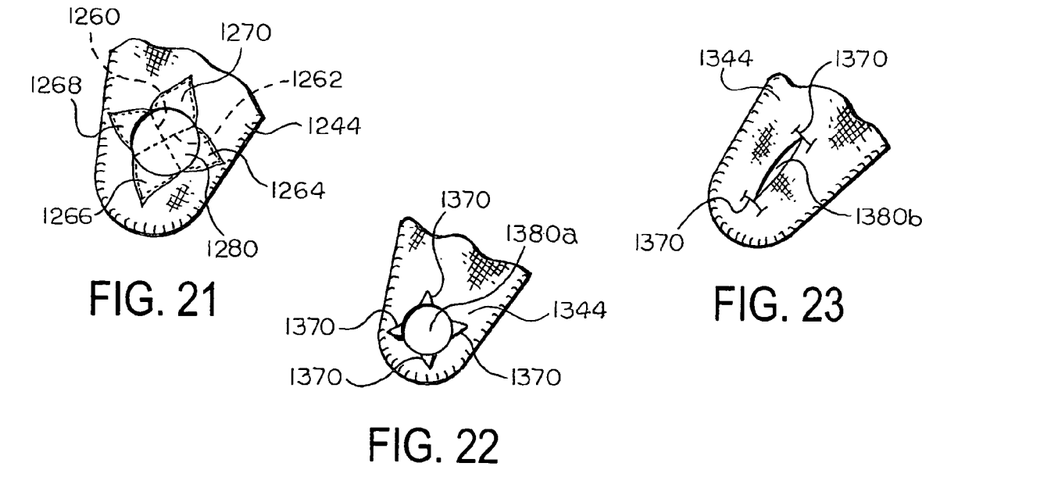
FIG. 21 is a magnified view of a valve leaflet with cut lines illustrating the formation of an opening in the leaflet.
FIG. 22 is a magnified view of a valve leaflet of a medical device according to an embodiment of the invention.
FIG. 23 is a magnified view of a valve leaflet of a medical device according to an embodiment of the invention.

FIG. 21 illustrates a method of forming an opening 1280 for allowing a controlled amount of retrograde flow to flow through a medical device according to the invention. Two cuts are made in the valve leaflet 1244 along intersecting lines 1260, 1262. The resulting flaps 1264, 1266, 1268, 1270 are folded back and can be secured to the valve leaflet 1244 by any suitable technique, or can be trimmed away.

The valve leaflet can be reinforced at one or more locations along the perimeter of the opening that permits a controlled amount of retrograde flow to flow through the medical device. In use, the opening will be exposed to a variety of forces in a dynamic environment. A reinforcement may increase the durability of the valve leaflet at the location of the opening by preventing tearing or other unintended expansion of the opening.

Any suitable means for reinforcing the valve leaflet can be used. The liners, such as the exemplary grommet described and illustrated herein, are a suitable reinforcement. Also, as illustrated in FIGS. 22 and 23, one or more sutures 1370 can be placed on the valve leaflet 1344 adjacent the opening that permits a controlled amount of retrograde flow through the device. The suture(s) 1370 can be drawn tight to gather a portion of the leaflet 1344. In the embodiment illustrated in FIG. 22, the sutures 1370 are placed at various locations around a circular opening 1380a. In FIG. 23, the sutures 1370 are placed at respective ends of a slit-like opening 1380b.

The preceding provides a detailed description of exemplary embodiments of the invention and includes the best mode for practicing the invention. The description of embodiments is intended only to enable one of ordinary skill in the art to make and use the invention, and is not intended to limit the invention in any manner.

We claim:

1. An implantable medical device that provides a valve for regulating fluid flow through a body vessel, comprising:
   a support frame having radially compressed and radially expanded configurations; and
   at least one leaflet at least partially defining a valve orifice that regulates said fluid flow, the at least one leaflet having first and second edges and being moveable between a first position that permits said fluid flow in a first direction and a second position that substantially prevents said fluid flow in a second, opposite direction, the first edge attached to the support frame and the second edge being free of the support frame;
   wherein a portion of the support frame and the second edge of the at least one leaflet cooperatively define an opening that permits a controlled amount of fluid flow to pass through said medical device in the second, opposite direction, the opening having a size that remains substantially fixed in the first and second positions of the at least one leaflet and being spaced from the valve orifice along an axis of said implantable medical device.

2. The implantable medical device according to claim 1, wherein the support frame is a self-expandable support frame.

3. The implantable medical device according to claim 2, wherein the support frame is formed of a nickel-titanium alloy.

4. The implantable medical device according to claim 1, wherein the at least one leaflet is formed of a bioremodellable material.

5. The implantable medical device according to claim 4, wherein the bioremodellable material comprises an extracellular matrix material.

6. The implantable medical device according to claim 4, wherein the bioremodellable material comprises small intestine submucosa.

7. The implantable medical device according to claim 1, wherein the opening has a total open area; and
   wherein the total open area of the opening is sized to be less than the cross-sectional area of said body vessel at a desired point of treatment in said body vessel.

8. The implantable medical device according to claim 1, wherein the opening has a total open area; and
   wherein the total open area of the opening is sized to be less than about 50% of the cross-sectional area of said body vessel at a desired point of treatment in said body vessel.

9. The implantable medical device according to claim 1, wherein the opening has a total open area; and
   wherein the total open area of the opening is sized to be less than about 25% of the cross-sectional area of said body vessel at a desired point of treatment.

10. An implantable medical device that provides a valve for regulating fluid flow through a body vessel, comprising:
    a support frame having radially compressed and radially expanded configurations; and
    at least one leaflet at least partially defining a valve orifice that regulates said fluid flow, the at least one leaflet having first and second edges and being moveable between a first position that permits said fluid flow in a first direction and a second position that substantially prevents said fluid flow in a second, opposite direction, the first edge attached to the support frame and the second edge being free of the support frame;
    wherein a portion of the support frame and the second edge of the at least one leaflet cooperatively define an opening that permits a controlled amount of fluid flow to pass through said medical device in the second, opposite direction, the opening being spaced from the valve orifice along an axis of said implantable medical device; and
    at least one suture attaching the first edge of the at least one leaflet to the support frame.

11. An implantable medical device that provides a valve for regulating fluid flow through a body vessel, comprising:
    a support frame having radially compressed and radially expanded configurations; and
    at least one leaflet at least partially defining a valve orifice that regulates said fluid flow, the at least one leaflet having first and second edges and being moveable between a first position that permits said fluid flow in a first direction and a second position that substantially prevents said fluid flow in a second, opposite direction, the first edge attached to the support frame and the second edge being free of the support frame;
    wherein a portion of the support frame and the second edge of the at least one leaflet cooperatively define an opening that permits a controlled amount of fluid flow to pass through said medical device in the second, opposite direction, the opening being spaced from the valve orifice along an axis of said implantable medical device; and
    wherein the at least one leaflet comprises first and second leaflets.

* * * * *